US008609586B2

(12) United States Patent
Satchivi et al.

(10) Patent No.: US 8,609,586 B2
(45) **Date of Patent: *Dec. 17, 2013**

(54) SAFENING COMPOSITION OF 6-(TRISUBSTITUTED PHENYL)-4-AMINO-2-PYRIDINECARBOXYLATE HERBICIDES AND CLOQUINTOCET-MEXYL FOR CEREAL CROPS

(75) Inventors: Norbert M. Satchivi, Westfield, IN (US); Paul R. Schmitzer, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/620,905

(22) Filed: Nov. 18, 2009

(65) Prior Publication Data

US 2010/0130363 A1 May 27, 2010

Related U.S. Application Data

(60) Provisional application No. 61/117,330, filed on Nov. 24, 2008.

(51) Int. Cl.
*A01N 25/32* (2006.01)
*A01N 43/40* (2006.01)

(52) U.S. Cl.
USPC ............................ 504/105; 504/130; 504/260

(58) Field of Classification Search
None
See application file for complete search history.

(56) References Cited

U.S. PATENT DOCUMENTS

| | | | | |
|---|---|---|---|---|
| 4,902,340 | A * | 2/1990 | Hubele | 504/105 |
| 7,314,849 | B2 * | 1/2008 | Balko et al. | 504/244 |

FOREIGN PATENT DOCUMENTS

| | | | | |
|---|---|---|---|---|
| WO | WO9418836 | A1 | | 9/1994 |
| WO | WO2007/082098 | A2 | | 7/2007 |
| WO | WO-2007082098 | | * | 7/2007 |
| WO | WO2009/029516 | A2 | | 3/2009 |
| WO | WO2009/029518 | A2 | | 3/2009 |
| WO | WO-2009029518 | | * | 3/2009 |
| WO | WO2010/059671 | A2 | | 5/2010 |
| WO | WO2010/059676 | A2 | | 5/2010 |
| WO | WO2010/059680 | | | 5/2010 |
| WO | WO2010/006581 | A2 | | 6/2010 |

* cited by examiner

*Primary Examiner* — Alton Pryor
(74) *Attorney, Agent, or Firm* — Robert Chang; Craig E. Mixan

(57) ABSTRACT

Herbicidal injury caused by 6-(trisubstituted phenyl)-4-amino-2-pyridinecarboxylates in wheat and barley is reduced with the use of low rates of cloquintocet.

9 Claims, No Drawings

SAFENING COMPOSITION OF 6-(TRISUBSTITUTED PHENYL)-4-AMINO-2-PYRIDINECARBOXYLATE HERBICIDES AND CLOQUINTOCET-MEXYL FOR CEREAL CROPS

FIELD OF THE INVENTION

This application claims the benefit of U.S. Provisional Application Ser. No. 61/117,330 filed on Nov. 24, 2008. This invention concerns the safening of the herbicidal injury caused by 6-(trisubstituted phenyl)-4-amino-2-pyridinecarboxylates in cereal crops.

BACKGROUND OF THE INVENTION

When agrochemicals, such as plant protection agents and especially herbicides, are used, the cultivated plants may be damaged to a certain degree, depending on factors such as the dose of agrochemicals and their method of application, the species of cultivated plant, the nature of the soil and climatic conditions, for example, length of time of exposure to light, temperature and amounts of precipitation. Thus, it is known that cultivated plants which are to be protected from the adverse effect of undesirable plant growth may be damaged to a certain degree when an effective dose of herbicide is used. Various substances which are capable of specifically preventing the adverse effect of an herbicide on the cultivated plants, i.e. of protecting the cultivated plants without at the same time noticeably influencing the herbicidal action on weeds to be combated, have been proposed to solve this problem. However, it has been found that the antidotes proposed frequently have only a narrow field of use, i.e., a particular antidote is frequently suitable only for use with individual species of cultivated plants and/or for protecting the cultivated plants from individual herbicidal substances or classes of substances. It has also been found that the antidotes proposed frequently are used at rates higher than the rates of the individual herbicidal substance.

U.S. Pat. No. 7,314,849 B2 describes certain 6-(polysubstituted aryl)-4-amino-2-pyridinecarboxylate compounds and their use as herbicides. While certain of these compounds have been shown to be particularly effective herbicides for controlling undesirable vegetation in cereal crops, they have also been shown to produce slight amounts of damage to both wheat and barley at concentrations required to adequately control the undesirable vegetation. U.S. Pat. No. 7,314,849 B2 also describes the safening of the herbicidal injury with cloquintocet-mexyl at herbicide-to-safener ratio that lies within the range of between about 1:1 and about 1:4, i.e., at a ratio where the rate of safener is equal to or exceeds the rate of the herbicide.

SUMMARY OF THE INVENTION

It has now been found that, surprisingly, the phytotoxic effect of certain 6-(trisubstituted aryl)-4-amino-2-pyridinecarboxylate compounds, which have an auxinic mode of action, on wheat and barley, can be ameliorated by the use of quinolinyloxyacetate safeners at very low rates. The present invention concerns a method of protecting cereal crops from the harmful effects of a 6-(trisubstituted phenyl)-4-amino-2-pyridinecarboxylate herbicide of the formula (I)

(I)

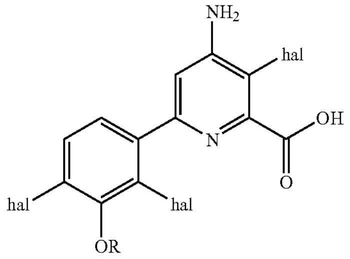

wherein hal represents F, Cl or Br, and R represents methyl or ethyl, and its agriculturally acceptable salt, ester and amide derivatives which comprises contacting wheat and barley with, or applying to the area under cultivation, a safener selected from the quinolinyloxyacetate family of chemicals in which the weight ratio of 6-(trisubstituted aryl)-4-amino-2-pyridinecarboxylate herbicide to quinolinyloxyacetate safener is between about 2:1 to about 64:1. The unexpectedly low rates of quinolinyloxyacetate prevent the herbicidal effects of a 6-(trisubstituted phenyl)-4-amino-2-pyridinecarboxylate herbicide of the formula (I) on cereal crops such as wheat and barley.

The present invention also concerns a composition for protecting wheat and barley from the harmful effects of a 6-(trisubstituted phenyl)-4-amino-2-pyridinecarboxylate herbicide of the formula (I)

(I)

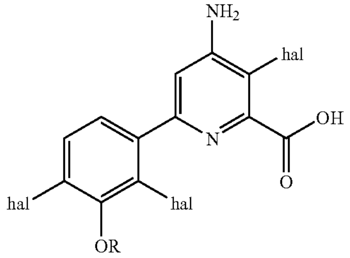

wherein hal represents F, Cl or Br, and R represents methyl or ethyl, and its agriculturally acceptable salt, ester and amide derivatives which comprises, in addition to the 6-(trisubstituted phenyl)-4-amino-2-pyridinecarboxylate herbicide, an active safener from the quinolinyloxyacetate family of chemicals in which the weight ratio of 6-(trisubstituted aryl)-4-amino-2-pyridinecarboxylate herbicide to quinolinyloxyacetate safener is between about 2:1 to about 64:1. In preferred compositions, the 6-(trisubstituted phenyl)-4-amino-2-pyridinecarboxylate herbicide is a 4-amino-3-chloro-6-(4-chloro-2-fluoro-3-methoxyphenyl)-2-pyridinecarboxylic acid derivative or a 4-amino-3-chloro-6-(2,4-dichloro-3-methoxyphenyl)-2-pyridinecarboxylic acid derivative. In preferred compositions, the quinolinyloxyacetate safener is cloquintocet, most preferably cloquintocet-mexyl.

It has been surprisingly found that the use of cloquintocet-mexyl at low rates in composition with a pyridinecarboxylate herbicide of the formula (I) exhibits a protecting effect against the phytotoxicity of the pyridinecarboxylate herbicide of formula (I) on spring and winter wheat (*Triticum aestivum* L; TRZAS, TRZAW), durum wheat (Triticum durum L; TRZDU) and spring and winter barley (*Hordeum*

*vulgare* L; HORVS, HORVW) at herbicide-to -safener ratios between 2:1 and 64:1 without losing the herbicidal effects on weeds such as cleavers (*Galium aparine* L; GALAP), purple deadnettle (*Lamium purpureum* L; LAMPU), kochia (*Kochia scoparia* L; KCHSC), scented mayweed (*Matricaria chamomila* L; MATCH), corn poppy (*Papaver rhoeas* L; PAPRH), wild buckwheat (*Polygonum convolvulus* L; POLCO), Russian thistle (*Salsola iberica* L; SASKR), chickweed (*Stellaria media* L; STEME), bird's-eye speedwell (*Veronica persica* L; VERPE), wild pansy (*Viola tricolor* L; VIOTR).

DETAILED DESCRIPTION OF THE INVENTION

The pyridinecarboxylic acids of formula I are a new class of compounds having herbicidal activity. A number of pyridinecarboxylic acid compounds are described in U.S. Pat. No. 7,314,849 B2, including 4-amino-3-chloro-6-(4-chloro-2-fluoro-3-methoxyphenyl)-pyridine-2-carboxylic acid. The pyridinecarboxylic acids of formula (I) control annual grass weeds and broadleaf weeds in wheat and barley but can be phytotoxic to wheat and barley at commercially herbicidal doses.

Safeners from the quinolinyloxyacetate family of chemicals are described in U.S. Pat. No. 4,902,340. The preferred safeners from the quinolinyloxyacetate family of chemicals are derivatives of cloquintocet, most preferably the mexyl ester. Cloquintocet is the common name for [(5-chloro-8-quinolinyl)oxy]acetic acid. Its safening activity is described in *The Pesticide Manual*, Fourteenth Edition, 2006. Cloquintocet is used as a safener in small grain cereals.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation. The term safener, as used herein, refers to a compound that selectively protects crop plants from herbicide damage without significantly reducing activity in target weed species.

Herbicidal activity is exhibited by the compounds when they are applied directly to the plant or to the locus of the plant via foliar, soil, or water application at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

Cultivated plants which are to be protected from the adverse effect of undesirable plant growth may be damaged to a certain degree when an effective dose of herbicides is used. Safening means preventing the adverse effect of an herbicide on the cultivated plants, i.e., protecting the cultivated plants without, at the same time, noticeably influencing the herbicidal action on weeds to be combated.

In the composition of this invention, the weight ratio of the pyridinecarboxylic acid of formula (I) to the safener at which the herbicidal effect on the cultivated plant is prevented lies within the range of between about 2:1 and about 64:1. Preferably, the weight ratio of the pyridinecarboxylic acid of formula (I) to the safener at which the herbicidal effect on the cultivated plant is prevented lies within the range of between about 4:1 and about 32:1.

The rate at which the safened composition is applied will depend upon the particular type of weed to be controlled, the degree of control required, and the timing and method of application. In general, the composition of the invention can be applied at an application rate of between about 0.8 grams per hectare (g/ha) and about 350 g/ha based on the total amount of pyridinecarboxylic acid of formula (I) and safener in the composition. In an especially preferred embodiment of the invention, cloquintocet is applied at a rate between about 0.273 g/ha and about 70 g/ha and the pyridinecarboxylic acid of formula (I) component is applied at a rate between about 0.55 g/ha and about 280 g/ha.

The pyridinecarboxylic acid of formula (I) and the safener of the present invention can be applied either separately or together as part of a multipart herbicidal system.

The herbicide-safener mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the safened composition of the present invention include: 2,4-D esters and amines, acetochlor, acifluorfen, aclonifen, AE0172747, alachlor, amidosulfuron, aminocyclopyrachlor, aminotriazole, ammonium thiocyanate, anilifos, atrazine, AVH 301, azimsulfuron, benfuresate, bensulfuron-methyl, bentazone, benthiocarb, benzobicyclon, bifenox, bispyribac-sodium, bromacil, bromoxynil, butachlor, butafenacil, butralin, cafenstrole, carbetamide, carfentrazone-ethyl, chlorflurenol, chlorimuron, chlorpropham, cinosulfuron, clethodim, clomazone, clopyralid, cloransulam-methyl, cyclosulfamuron, cycloxydim, cyhalofop-butyl, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ET-751, ethoxysulfuron, ethbenzanid, F7967, fenoxaprop, fenoxaprop-ethyl, fenoxaprop-ethyl+isoxadifen-ethyl, fentrazamide, flazasulfuron, florasulam, fluazifop, fluazifop-P-butyl, flucetosulfuron, flufenacet, flufenpyr-ethyl, flumetsulam, flumiclorac-pentyl, flumioxazin, fluometuron, flupyrsulfuron, fluoroxypyr, fomesafen, foramsulfuron, fumiclorac, glufosinate, glufosinate-ammonium, glyphosate, halosulfuron, haloxyfop-methyl, haloxyfop-R, imazamethabenz, imazamox, imazapic, imazapyr, imazaquin, imazethapyr, imazosulfuron, indanofan, iodosulfuron, ioxynil, IR 5790, isoproturon, isoxaben, isoxaflutole, KUH-021, lactofen, linuron, MCPA, MCPA ester & amine, mecoprop-P, mefenacet, mesosulfuron, mesotrione, metamifop, metolachlor, metosulam, metribuzin, metsulfuron, molinate, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, penoxsulam, pentoxazone, pethoxamid, picloram, picolinafen, piperophos, pretilachlor, profoxydim, propachlor, propanil, propyzamide, prosulfocarb, prosulfuron, pyraclonil, pyrasulfotole, pyrazogyl, pyrazosulfuron, pyribenzoxim, pyriftalid, pyriminobac-methyl, primisulfuron, pyroxsulam, quinclorac, quizalofop-ethyl-D, S-3252, saflufenacil, sethoxydim, simazine, SL-0401, SL-0402, s-metolachlor, sulcotrione, sulfentrazone, sulfosate, tebuthiuron, terbacil, TH-547, thiazopyr, thiobencarb, triclopyr, triclopyr esters and amine, trifluralin and tritosulfuron.

The safened composition of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the herbicide-safener mixture of the present invention in combination with herbicides that are selective for the crop being treated and which complement the spectrum of weeds controlled by these compounds at the application rate employed. It is further generally preferred to apply the safened composition of the present invention and other complementary herbicides at the same time, either as a combination formulation or as a tank mix.

In practice, it is preferable to use the safened composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8E0); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzene-sulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cotton seed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicide-safener mixture of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, or irrigation water, and by other conventional means known to those skilled in the art.

The following examples illustrate the present invention.

Evaluation of Postemergence Herbicidal Safening in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Weighed amounts of esters (methyl) or salts (TEA [triethylammonium], potassium [K]) of 4-amino-3-chloro-6-(4-chloro-2-fluoro-3-methoxyphenyl)pyridine-2-carboxylic acid (Compound 1) were dissolved in a volume of 97:3 volume/volume (v/v) acetone/dimethylsulfoxide (DMSO) to obtain stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 mL application volume at a rate of 187 liters per hectare (L/ha). Stocks solutions of the safeners were prepared following the same procedure. Spray solutions of the safeners and experimental compound mixtures were prepared by adding the appropriate volume of both stock solutions to the appropriate amount of dilution solution to form a 12 mL spray solution with active ingredients in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected}=A+B-(A\times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 1 through Table 7.

TABLE 1

Safening Activity of Herbicidal Compositions on Wheat and Barley

| Application Rate (g/ha) | | | | | | | | | | | | | | | | | | | | | | |
|---|---|---|---|---|---|---|---|---|---|---|---|---|---|---|---|---|---|---|---|---|---|---|
| Compound I Methyl Ester | Cloquintocet-mexyl | Herbicide: Safener Ratio | HORVS | | TRZAS | | TRZAW | | HORVW | | GALAP | | KCHSC | | MATCH | | SASKR | | VERPE | | VIOTR | |
| | | | Ob | Ex | Ob | Ex | Ob | Ex | Ob | Ex | Ob | Ex | Ob | Ex | Ob | Ex | Ob | Ex | Ob | Ex | Ob | Ex |
| 8.75 | 0 | — | 22 | — | 13 | — | | | | | | | | | | | | | | | | |
| 35 | 0 | — | 38 | — | 43 | — | | | | | | | | | | | | | | | | |
| 70 | 0 | — | | — | 25 | — | | | | | | | | | | | | | | | | |
| 140 | 0 | — | 42 | — | 37 | — | 32 | — | 42 | — | 100 | — | 100 | — | 82 | — | 91 | — | 91 | — | 67 | — |
| 0 | 1.1 | — | 0 | — | 0 | — | | | | | | | 0 | — | 0 | — | 0 | — | 0 | — | 0 | — |
| 0 | 2.2 | — | 0 | — | 0 | — | | | | | | | 0 | — | 0 | — | 0 | — | 0 | — | 0 | — |
| 0 | 4.4 | — | 0 | — | 0 | — | | | | | | | 0 | — | 0 | — | 0 | — | 0 | — | 0 | — |
| 0 | 8.75 | — | 0 | — | 0 | — | | | | | | | 0 | — | 0 | — | 0 | — | 0 | — | 0 | — |
| 0 | 17.5 | — | 0 | — | 0 | — | | | | | | | 0 | — | 0 | — | 0 | — | 0 | — | 0 | — |
| 0 | 35 | — | 0 | — | 0 | — | 0 | — | 0 | — | | | 0 | — | 0 | — | 0 | — | 0 | — | 0 | — |
| 0 | 70 | — | 0 | — | 0 | — | 0 | — | 0 | — | | | 0 | — | 0 | — | 0 | — | 0 | — | 0 | — |
| 8.75 | 1.1 | 8:1 | 0 | 22 | 1 | 13 | | | | | | | | | | | | | | | | |
| 35 | 1.1 | 31:1 | 2 | 38 | 3 | 43 | | | | | | | | | | | | | | | | |
| 70 | 1.1 | 64:1 | | | 2 | 25 | | | | | | | | | | | | | | | | |
| 140 | 2.2 | 64:1 | | | 10 | 37 | | | | | | | | | | | | | | | | |
| 140 | 4.4 | 32:1 | | | 7 | 37 | | | | | | | | | | | | | | | | |
| 140 | 8.75 | 16:1 | 0 | 42 | 2 | 37 | | | | | | | 100 | 100 | 86 | 82 | 88 | 91 | 93 | 91 | 62 | 67 |
| 140 | 17.5 | 8:1 | 0 | 42 | 2 | 37 | | | | | | | 100 | 100 | 89 | 82 | 89 | 91 | 92 | 91 | 58 | 67 |
| 140 | 35 | 4:1 | 0 | 42 | 3 | 37 | 5 | 32 | 0 | 42 | 100 | 100 | 100 | 100 | 89 | 82 | 88 | 91 | 91 | 91 | 60 | 67 |
| 140 | 70 | 2:1 | 0 | 42 | 3 | 37 | 5 | 32 | 0 | 42 | 100 | 100 | 100 | 100 | 83 | 82 | 89 | 91 | 86 | 91 | 40 | 67 |

TABLE 2

Safening Activity of Herbicidal Compositions on Wheat and Barley

| Application Rate (g/ha) | | | | | | | | | | | | | | | | |
|---|---|---|---|---|---|---|---|---|---|---|---|---|---|---|---|---|
| Compound (I) K-salt | Cloquintocet-mexyl | Herbicide: Safener Ratio | HORVS | | TRZAS | | KCHSC | | MATCH | | SASKR | | VERPE | | VIOTR | |
| | | | Ob | Ex | Ob | Ex | Ob | Ex | Ob | Ex | Ob | Ex | Ob | Ex | Ob | Ex |
| 8.75 | 0 | | 25 | — | 15 | — | | — | | — | | — | | — | | — |
| 35 | 0 | | 38 | — | 43 | — | | — | | — | | — | | — | | — |
| 70 | 0 | | | — | 11 | — | | — | | — | | — | | — | | — |
| 140 | 0 | | 45 | — | 52 | — | 100 | — | 88 | — | 87 | — | 87 | — | 63 | — |
| 0 | 1.0937 | | 0 | — | 0 | — | 0 | — | 0 | — | 0 | — | 0 | — | 0 | — |

TABLE 2-continued

Safening Activity of Herbicidal Compositions on Wheat and Barley

| Application Rate (g/ha) Compound (I) K-salt | Application Rate (g/ha) Cloquintocet-mexyl | Herbicide: Safener Ratio | HORVS Ob | HORVS Ex | TRZAS Ob | TRZAS Ex | KCHSC Ob | KCHSC Ex | MATCH Ob | MATCH Ex | SASKR Ob | SASKR Ex | VERPE Ob | VERPE Ex | VIOTR Ob | VIOTR Ex |
|---|---|---|---|---|---|---|---|---|---|---|---|---|---|---|---|---|
| 0 | 2.1875 | | 0 | — | 0 | — | 0 | — | 0 | — | 0 | — | 0 | — | 0 | — |
| 0 | 4.375 | | 0 | — | 0 | — | 0 | — | 0 | — | 0 | — | 0 | — | 0 | — |
| 0 | 8.75 | | 0 | — | 0 | — | 0 | — | 0 | — | 0 | — | 0 | — | 0 | — |
| 0 | 17.5 | | 0 | — | 0 | — | 0 | — | 0 | — | 0 | — | 0 | — | 0 | — |
| 0 | 35 | | 0 | — | 0 | — | 0 | — | 0 | — | 0 | — | 0 | — | 0 | — |
| 0 | 70 | | 0 | — | 0 | — | 0 | — | 0 | — | 0 | — | 0 | — | 0 | — |
| 8.75 | 1.0937 | 8:1 | 2 | 25 | 1 | 15 | | | | | | | | | | |
| 35 | 1.0937 | 32:1 | 3 | 38 | 2 | 43 | | | | | | | | | | |
| 70 | 1.0937 | 64:1 | | | 0 | 11 | | | | | | | | | | |
| 140 | 2.1875 | 64:1 | | | 8 | 52 | | | | | | | | | | |
| 140 | 4.375 | 32:1 | | | 10 | 52 | | | | | | | | | | |
| 140 | 8.75 | 16:1 | 2 | 45 | 0 | 52 | 100 | 100 | 91 | 88 | 87 | 87 | 89 | 87 | 50 | 63 |
| 140 | 17.5 | 8:1 | 0 | 45 | 0 | 52 | 100 | 100 | 89 | 88 | 90 | 87 | 90 | 87 | 50 | 63 |
| 140 | 35 | 4:1 | 0 | 45 | 0 | 52 | 100 | 100 | 85 | 88 | 90 | 87 | 90 | 87 | 43 | 63 |
| 140 | 70 | 2:1 | 0 | 45 | 0 | 52 | 100 | 100 | 90 | 88 | 88 | 87 | 92 | 87 | 38 | 63 |

TABLE 3a

Safening Activity of Herbicidal Compositions on Wheat and Barley

| Application Rate (g/ha) Compound (I) TEA salt | Application Rate (g/ha) Cloquintocet-mexyl | Herbicide: Safener Ratio | HORVS Ob | HORVS Ex | TRZAS Ob | TRZAS Ex | TRZAW Ob | TRZAW Ex | HORVW Ob | HORVW Ex | TRZDU Ob | TRZDU Ex | GALAP Ob | GALAP Ex | KCHSC Ob | KCHSC Ex | LAMPU Ob | LAMPU Ex |
|---|---|---|---|---|---|---|---|---|---|---|---|---|---|---|---|---|---|---|
| 8.75 | 0 | | 25 | — | 5 | — | | — | | | | — | | — | | — | | — |
| 35 | 0 | | 23 | — | 15 | — | | — | | | | — | | — | | — | | — |
| 70 | 0 | | | — | 10 | — | | — | | | | — | | — | | — | | — |
| 140 | 0 | | 23 | — | 27 | — | 24 | — | 15 | | 10 | — | 100 | — | 95 | — | 98 | — |
| 0 | 1.1 | | 0 | — | 0 | — | 0 | — | | | 0 | — | 0 | — | 0 | — | 0 | — |
| 0 | 2.2 | | 0 | — | 0 | — | 0 | — | | | 0 | — | 0 | — | 0 | — | 0 | — |
| 0 | 4.4 | | 0 | — | 0 | — | 0 | — | | | 0 | — | 0 | — | 0 | — | 0 | — |
| 0 | 8.75 | | 0 | — | 0 | — | 0 | — | | | 0 | — | 0 | — | 0 | — | 0 | — |
| 0 | 17.5 | | 0 | — | 0 | — | 0 | — | | | 0 | — | 0 | — | 0 | — | 0 | — |
| 0 | 35 | | 0 | — | 0 | — | 0 | — | 0 | — | 0 | — | 0 | — | 0 | — | 0 | — |
| 0 | 70 | | 0 | — | 0 | — | 0 | — | 0 | — | 0 | — | 0 | — | 0 | — | 0 | — |
| 8.75 | 1.1 | 8:1 | 3 | 25 | 1 | 5 | | | | | | | | | | | | |
| 35 | 1.1 | 31:1 | 3 | 23 | 0 | 15 | | | | | | | | | | | | |
| 70 | 1.1 | 64:1 | | | 0 | 10 | | | | | | | | | | | | |
| 140 | 2.2 | 64:1 | | | 6 | 27 | | | | | | | | | | | | |
| 140 | 4.4 | 32:1 | | | 6 | 27 | | | | | | | | | | | | |
| 140 | 8.75 | 16:1 | 3 | 23 | 0 | 27 | | | | | | | | | 100 | 95 | | |
| 140 | 17.5 | 8:1 | 1 | 23 | 0 | 27 | 0 | 24 | | | 0 | 10 | 100 | 100 | 89 | 95 | 100 | 98 |
| 140 | 35 | 4:1 | 1 | 23 | 0 | 27 | 3 | 24 | 0 | 15 | 0 | 10 | 100 | 100 | 97 | 95 | 100 | 98 |
| 140 | 70 | 2:1 | 1 | 23 | 0 | 27 | 0 | 24 | 0 | 15 | 0 | 10 | 100 | 100 | 97 | 95 | 100 | 98 |

TABLE 3b

Safening Activity of Herbicidal Compositions on Wheat and Barley

| Application Rate (g/ha) Compound (I) TEA salt | Application Rate (g/ha) Cloquintocet-mexyl | Herbicide: Safener Ratio | MATCH Ob | MATCH Ex | PAPRH Ob | PAPRH Ex | POLCO Ob | POLCO Ex | SASKR Ob | SASKR Ex | STEME Ob | STEME Ex | VERPE Ob | VERPE Ex | VIOTR Ob | VIOTR Ex |
|---|---|---|---|---|---|---|---|---|---|---|---|---|---|---|---|---|
| 8.75 | 0 | | | — | | — | | — | | — | | — | | — | | — |
| 35 | 0 | | | — | | — | | — | | — | | — | | — | | — |
| 70 | 0 | | | — | | — | | — | | — | | — | | — | | — |
| 140 | 0 | | 84 | — | 100 | — | 100 | — | 86 | — | 88 | — | 89 | — | 66 | — |
| 0 | 1.1 | | 0 | — | 0 | — | 0 | — | 0 | — | 0 | — | 0 | — | 0 | — |
| 0 | 2.2 | | 0 | — | 0 | — | 0 | — | 0 | — | 0 | — | 0 | — | 0 | — |
| 0 | 4.4 | | 0 | — | 0 | — | 0 | — | 0 | — | 0 | — | 0 | — | 0 | — |
| 0 | 8.75 | | 0 | — | 0 | — | 0 | — | 0 | — | 0 | — | 0 | — | 0 | — |

TABLE 3b-continued

Safening Activity of Herbicidal Compositions on Wheat and Barley

| Application Rate (g/ha) | | | | | | | | | | | | | | | | |
|---|---|---|---|---|---|---|---|---|---|---|---|---|---|---|---|---|
| Compound (I) TEA | Cloquintocet- | Herbicide: Safener | MATCH | | PAPRH | | POLCO | | SASKR | | STEME | | VERPE | | VIOTR | |
| salt | mexyl | Ratio | Ob | Ex | Ob | Ex | Ob | Ex | Ob | Ex | Ob | Ex | Ob | Ex | Ob | Ex |
| 0 | 17.5 | | 0 | — | 0 | — | 0 | — | 0 | — | 0 | — | 0 | — | 0 | — |
| 0 | 35 | | 0 | — | 0 | — | 0 | — | 0 | — | 0 | — | 0 | — | 0 | — |
| 0 | 70 | | 0 | — | 0 | — | 0 | — | 0 | — | 0 | — | 0 | — | 0 | — |
| 8.75 | 1.1 | 8:1 | | | | | | | | | | | | | | |
| 35 | 1.1 | 32:1 | | | | | | | | | | | | | | |
| 70 | 1.1 | 64:1 | | | | | | | | | | | | | | |
| 140 | 2.2 | 64:1 | | | | | | | | | | | | | | |
| 140 | 4.4 | 32:1 | | | | | | | | | | | | | | |
| 140 | 8.75 | 16:1 | 86 | 84 | | | | | 88 | 86 | | | 89 | 89 | 62 | 66 |
| 140 | 17.5 | 8:1 | 83 | 84 | 100 | 100 | 100 | 100 | 91 | 86 | 95 | 88 | 90 | 89 | 40 | 66 |
| 140 | 35 | 4:1 | 76 | 84 | 100 | 100 | 100 | 100 | 87 | 86 | 100 | 88 | 90 | 89 | 34 | 66 |
| 140 | 70 | 2:1 | 88 | 84 | 100 | 100 | 100 | 100 | 88 | 86 | 80 | 88 | 89 | 89 | 29 | 66 |

TABLE 4

Safening Activity of Herbicidal Compositions on Wheat and Barley

| Application Rate (g/ha) | | | | | | | | | | |
|---|---|---|---|---|---|---|---|---|---|---|
| Compound (I) Methyl | Cloquintocet- | Herbicide:Safener | TRZAS | | HORVS | | LAMPU | | PAPRH | |
| ester | acid | Ratio | Ob | Ex | Ob | Ex | Ob | Ex | Ob | Ex |
| 35 | 0 | | 45 | | 43 | | 100 | | 97 | |
| 0 | 0.55 | | 0 | — | 0 | — | 0 | — | 0 | — |
| 0 | 1.1 | | 0 | — | 0 | — | 0 | — | 0 | — |
| 0 | 2.2 | | 0 | — | 0 | — | 0 | — | 0 | — |
| 0 | 4.4 | | 0 | — | 0 | — | 0 | — | 0 | — |
| 35 | 0.55 | 64:1 | 0 | 45 | 2 | 43 | 100 | 100 | 100 | 97 |
| 35 | 1.1 | 32:1 | 0 | 45 | 1 | 43 | 100 | 100 | 100 | 97 |
| 35 | 2.2 | 16:1 | 0 | 45 | 0 | 43 | 100 | 100 | 100 | 97 |
| 35 | 4.4 | 8:1 | 0 | 45 | 0 | 43 | 100 | 100 | 99 | 97 |

TABLE 5

Safening Activity of Herbicidal Compositions on Wheat and Barley

| Application Rate (g/ha) | | | | | | | | | | |
|---|---|---|---|---|---|---|---|---|---|---|
| Compound (I) Methyl | Cloquintocet- triisopropylamine | Herbicide:Safener | TRZAS | | HORVS | | LAMPU | | PAPRH | |
| ester | salt | Ratio | Ob | Ex | Ob | Ex | Ob | Ex | Ob | Ex |
| 35 | 0 | | 45 | | 43 | | 100 | | 97 | |
| 0 | 0.55 | | 0 | — | 0 | — | 0 | — | 0 | — |
| 0 | 1.1 | | 0 | — | 0 | — | 0 | — | 0 | — |
| 0 | 2.2 | | 0 | — | 0 | — | 0 | — | 0 | — |
| 0 | 4.4 | | 0 | — | 0 | — | 0 | — | 0 | — |
| 35 | 0.55 | 64:1 | 0 | 45 | 2 | 43 | 100 | 100 | 100 | 97 |
| 35 | 1.1 | 32:1 | 0 | 45 | 2 | 43 | 100 | 100 | 100 | 97 |
| 35 | 2.2 | 16:1 | 0 | 45 | 0 | 43 | 100 | 100 | 100 | 97 |
| 35 | 4.4 | 8:1 | 0 | 45 | 0 | 43 | 100 | 100 | 100 | 97 |

TABLE 6

Safening Activity of Herbicidal Compositions on Wheat and Barley

| Application Rate (g/ha) Compound (I) Methyl ester | Application Rate (g/ha) Cloquintocet-triethanolamine salt | Herbicide:Safener Ratio | TRZAS Ob | TRZAS Ex | HORVS Ob | HORVS Ex | LAMPU Ob | LAMPU Ex | PAPRH Ob | PAPRH Ex |
|---|---|---|---|---|---|---|---|---|---|---|
| 35 | 0 | | 45 | | 43 | | 100 | | 97 | |
| 0 | 0.55 | | 0 | — | 0 | — | 0 | — | 0 | — |
| 0 | 1.1 | | 0 | — | 0 | — | 0 | — | 0 | — |
| 0 | 2.2 | | 0 | — | 0 | — | 0 | — | 0 | — |
| 0 | 4.4 | | 0 | — | 0 | — | 0 | — | 0 | — |
| 35 | 0.55 | 64:1 | 0 | 45 | 0 | 43 | 100 | 100 | 100 | 97 |
| 35 | 1.1 | 32:1 | 0 | 45 | 0 | 43 | 100 | 100 | 100 | 97 |
| 35 | 2.2 | 16:1 | 0 | 45 | 0 | 43 | 100 | 100 | 100 | 97 |
| 35 | 4.4 | 8:1 | 0 | 45 | 0 | 43 | 100 | 100 | 100 | 97 |

TABLE 7

Safening Activity of Herbicidal Compositions on Wheat and Barley

| Application Rate (g/ha) Compound (I) Methyl ester | Application Rate (g/ha) Cloquintocet-dimethylamine salt | Herbicide:Safener Ratio | TRZAS Ob | TRZAS Ex | HORVS Ob | HORVS Ex | LAMPU Ob | LAMPU Ex | PAPRH Ob | PAPRH Ex |
|---|---|---|---|---|---|---|---|---|---|---|
| 35 | 0 | | 45 | | 43 | | 100 | | 97 | |
| 0 | 0.55 | | 0 | — | 0 | — | 0 | — | 0 | — |
| 0 | 1.1 | | 0 | — | 0 | — | 0 | — | 0 | — |
| 0 | 2.2 | | 0 | — | 0 | — | 0 | — | 0 | — |
| 0 | 4.4 | | 0 | — | 0 | — | 0 | — | 0 | — |
| 35 | 0.55 | 64:1 | 0 | 45 | 0 | 43 | 100 | 100 | 100 | 97 |
| 35 | 1.1 | 32:1 | 0 | 45 | 0 | 43 | 100 | 100 | 97 | 97 |
| 35 | 2.2 | 16:1 | 0 | 45 | 0 | 43 | 100 | 100 | 99 | 97 |
| 35 | 4.4 | 8:1 | 0 | | 0 | 43 | 100 | 100 | 99 | 97 |

TRZAS = *Triticum aestivum* (spring wheat)
TRZAW = *Triticum aestivum* (winter wheat)
TRZDU = *Triticum durum* (durum wheat)
HORVS = *Hordeum vulgare* (spring barley)
HORVW = *Hordeum vulgare* (winter barley)
GALAP = *Galium aparine* (cleavers)
KCHSC = *Kochia scoparia* (*kochia*)
LAMPU = *Lamium purpureum* (purple deadnettle)
Ob = Observed values
g/ha = grams per hectare
MATCH = *Matricaria chamomila* (scented mayweed)
PAPRH = *Papaver rhoeas* (corn poppy)
POLCO = *Polygonum convolvulus* (wild buckwheat)
SASKR = *Salsola iberica* (Russian thistle)
STEME = *Stellaria media* (common chickweed)
VERPE = *Veronica persica* (bird's-eye speedwell)
VIOTR = *Viola tricolor* (wild pansy)
Ex = Expected values

What is claimed is:

1. A composition for protecting wheat and barley from the harmful effects of a 6-(trisubstituted phenyl)-4-amino-2-pyridine-carboxylate herbicide of the formula (I)

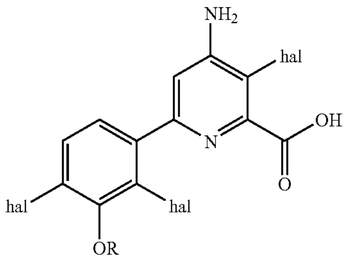

(I)

wherein hal represents F, Cl or Br, and R represents methyl or ethyl, and its agriculturally acceptable salt, ester and amide derivatives which comprises, in addition to the 6-(trisubstituted phenyl)-4-amino-2-pyridinecarboxylate herbicide, a safener from the quinolinyloxyacetate family of chemicals in which the weight ratio of 6-(trisubstituted aryl)-4-amino-2-pyridinecarboxylate herbicide to quinolinyloxyacetate safener is between 2:1 to about 64:1.

2. The composition of claim 1 in which the 6-(trisubstituted phenyl)-4-amino-2-pyridinecarboxylate herbicide is a 4-amino-3-chloro-6-(4-chloro-2-fluoro-3-methoxyphenyl)-2-pyridinecarboxylic acid derivative or a 4-amino-3-chloro-6-(2,4-dichloro-3-methoxyphenyl)-2-pyridinecarboxylic acid derivative.

3. The composition of claim 1 in which the safener is cloquintocet mexyl.

4. The composition of claim 1 in which the weight ratio of the 6-(trisubstituted phenyl)-4-amino-2-pyridinecarboxylate herbicide to the safener is between 4:1 and 32:1.

5. The composition of claim 1, in which the weight ratio of the 6-(trisubstituted phenyl)-4-amino-2-pyridinecarboxylate herbicide to the safener is from greater than 32:1 to 64:1.

6. The composition of claim 5, in which the safener is cloquintocet mexyl.

7. A method of protecting wheat and barley from the harmful effects of a 6-(trisubstituted phenyl)-4-amino-2-pyridinecarboxylate herbicide of the formula (I)

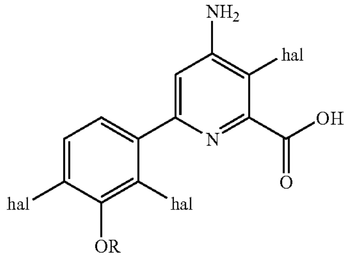

(I)

wherein hal represents F, Cl or Br, and R represents methyl or ethyl, and its agriculturally acceptable salt, ester and amide derivatives which comprises contacting the wheat and barley with, or applying to the area under cultivation, a safener selected from the quinolinyloxyacetate family of chemicals in which the weight ratio of 6-(trisubstituted aryl)-4-amino-2-pyridinecarboxylate herbicide to quinolinyloxyacetate safener is between 2:1 to 64:1.

8. The method of claim 7, in which the weight ratio of 6-(trisubstituted aryl) -4-amino-2-pyridinecarboxylate herbicide to quinolinyloxyacetate safener is from greater than 32:1 to 64:1.

9. The method of claim 8, in which the safener is cloquintocet mexyl.

* * * * *